United States Patent [19]

Matsuishi et al.

[11] 4,399,304

[45] Aug. 16, 1983

[54] L-PHENYLALANINE ½ SULFATE AND ITS USE

[75] Inventors: Tsutomu Matsuishi; Hiromasa Maruyama, both of Saga; Toshio Kitahara, Yokosuka; Akemi Kabashima; Ryuta Toyomasu, both of Saga, all of Japan

[73] Assignee: Ajinomoto Company Incorporated, Tokyo, Japan

[21] Appl. No.: 291,914

[22] Filed: Aug. 11, 1981

Related U.S. Application Data

[62] Division of Ser. No. 210,349, Nov. 25, 1980, abandoned.

[30] Foreign Application Priority Data

Dec. 5, 1979 [JP] Japan ................................. 54-157562

[51] Int. Cl.$^3$ .......................................... C07C 101/08
[52] U.S. Cl. .................................................. 562/445
[58] Field of Search ................ 562/401, 402, 443, 445

[56] References Cited

U.S. PATENT DOCUMENTS

| | | | |
|---|---|---|---|
| 2,790,001 | 4/1957 | Purvis ................................. | 562/402 |
| 3,030,380 | 4/1962 | Weygand et al. ................... | 562/443 |
| 3,830,836 | 8/1974 | Asai et al. ........................... | 562/402 |
| 3,994,962 | 11/1976 | Shirai et al. ........................ | 562/401 |
| 4,260,684 | 4/1981 | Schutt ................................. | 562/401 |

FOREIGN PATENT DOCUMENTS 53-79837  7/1978  Japan .................................. 562/402

OTHER PUBLICATIONS

Ogata et al., Chem. Abst., vol. 84 #106115r (1976).

*Primary Examiner*—James H. Reamer
*Attorney, Agent, or Firm*—Oblon, Fisher, Spivak, McClelland & Maier

[57] ABSTRACT

The present invention relates to L-phenylalanine ½ sulfate and its use in the purification of L-phenylalanine from fermentation broths. When the salt is crystallized from a fermentation broth of L-phenylalanine or a solution produced during an intermediate process of recovering L-phenylalanine from the fermentation broth, impurities derived from the fermentation broth are easily removed.

6 Claims, 5 Drawing Figures

L-PHENYLALANINE ½ SULFATE AND ITS USE

This is a division, of application Ser. No. 210,349, filed Nov. 25, 1980 now abandoned.

BACKGROUND OF THE INVENTION

1. Field of the Invention

This invention relates to the novel compound L-phenylalanine ½ sulfate and to a process for recovering L-phenylalanine (L-Phe) from a fermentation broth containing L-phenylalanine which employs crystallization of the ½ sulfate salt.

2. Description of the Prior Art

L-Phenylalanine has usually been recovered from L-phenylalanine-producing fermentation broths by treating the broth with an ion-exchange resin followed by repeated crystallization of the L-phenylalanine eluted from the ion-exchange resin. One of the problems of this method is the low rate at which impurities are removed in the crystallization steps. This low removal rate may be attributed to several factors including insufficient removal of mother liquor from the crystals, caused by the flake-like crystalline form of L-phenylalanine, and adsorption of colored substances and other impurities by the crystals because of strong van der Waals force between impurities and L-phenylalanine. Consequently, it is necessary to increase the number of crystallization steps. This, in turn, complicates the process of separating L-phenylalanine and lowers its yield.

SUMMARY OF THE INVENTION

Accordingly, one object of the present invention is to provide a process for producing pure L-phenylalanine from a fermentation broth that avoids the tendency of L-phenylalanine to absorb impurities during crystallization.

It is another object of the present invention to provide a process that avoids the excessive number of crystallization steps that have previously been required for the purification of L-phenylalanine.

These and other objects as will hereinafter be recognized from the ensuing discussions have been attained by providing a salt of L-phenylalanine, L-phenylalanine ½ sulfate, which may be either hydrated or anhydrous, which, when used in the process of separating L-phenylalanine from its fermentation broth, alleviates the problems previously encountered in the crystallization process and makes easy the removal of impurities normally present in the fermentation broth from L-phenylalanine. Namely, the present invention provides a novel salt, L-phenylalanine ½ sulfate, and a use thereof in a process for recovering L-phenylalanine, which comprises crystallizing L-phenylalanine ½ sulfate from a fermentation broth or a solution produced during an intermediate process of recovering L-phenylalanine from the fermentation broth.

DETAILED DESCRIPTION OF THE INVENTION

It was discovered that the objects of the invention can be achieved by forming the ½ sulfate salt of phenylalanine. The salt of the invention may be in an amorphous state or in a crystalline state. The crystalline state may be anhydrous or alternatively hydrated, for example, as the ½ hydrate of the salt.

L-Phenylalanine ½ sulfate ½ hydrate in the crystalline state has the following properties. The crystals used for the measurements of the properties were obtained in the experiment described in Example 1.

PHYSICAL PROPERTIES OF L-PHENYLALANINE ½ SULFATE ½ HYDRATE

1. Elemental Analysis

| | Calculated Value | Measured Value |
| --- | --- | --- |
| C | 48.42% | 48.41% |
| H | 5.87 | 5.96 |
| N | 6.27 | 6.32 |
| O | 32.25 | 32.00 |
| S | 7.18 | 7.30 |
| $H_2O$*[1] | 4.03 | 3.99 |
| $H_2SO_4$*[2] | 21.95 | 21.97 |

*[1]Karl-Fischer's method
*[2]Neutralization using NaOH

2. Infrared Spectra

Figure 1:
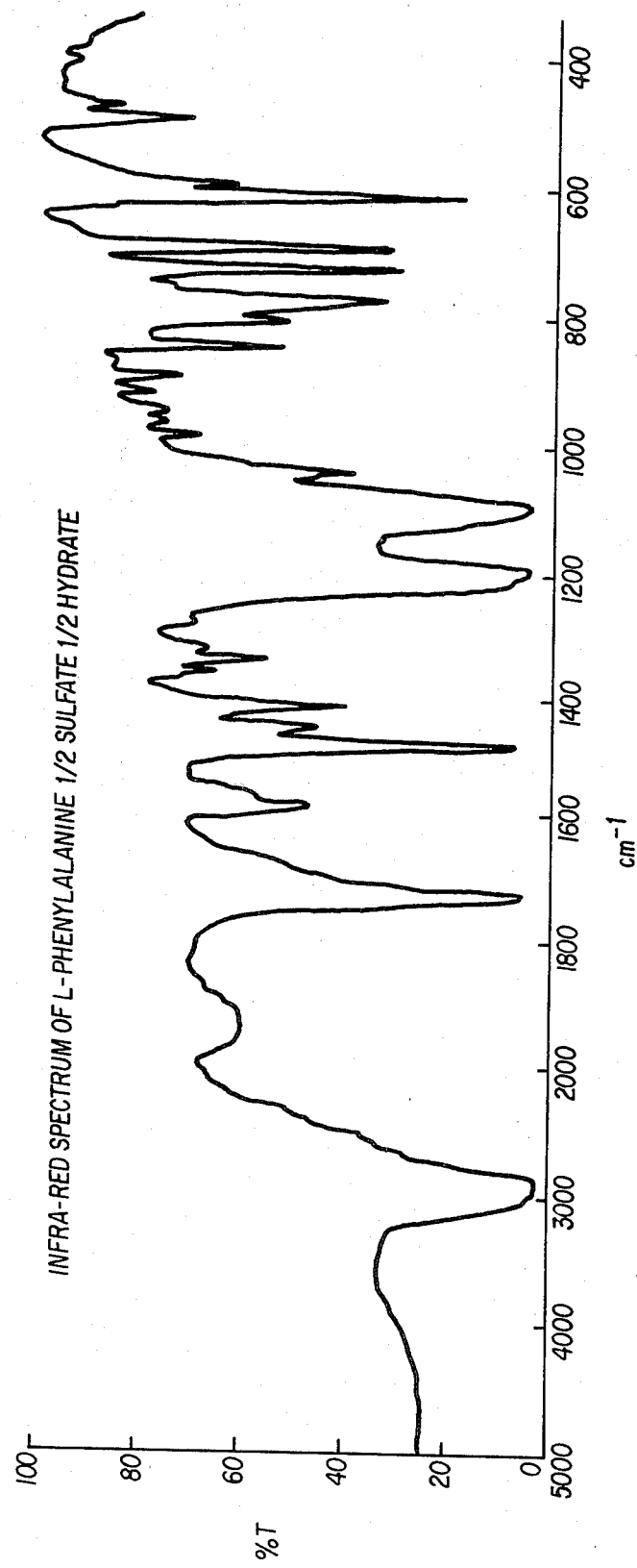

Infrared spectra of the crystals pelleted with potassium bromide are shown in FIG. 1.

3. Thermal Properties

Temperature of transformation: 93.5°–94° C.

Figure 2:
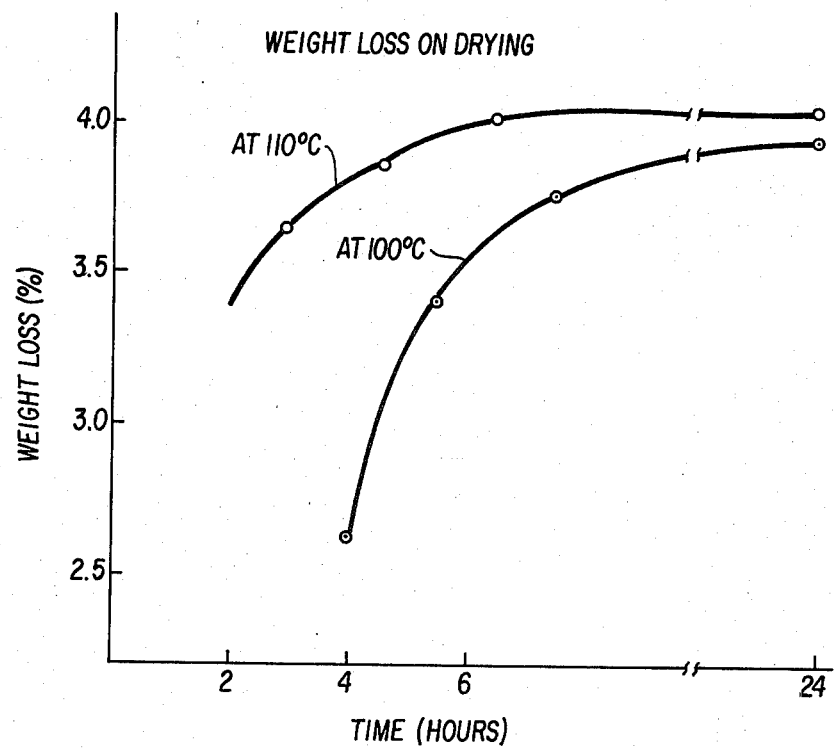

The reductions in weight at 100° C. and at 110° C. are shown in FIG. 2.

4. Optical Rotation $[\alpha]_D^{20} = -12.7°$ (C=2, $H_2O$)

The concentration term C expresses the number of grams of L-Phe.½ $H_2SO_4$.½ $H_2O$ per dl-solution.

5. Powder X-Ray Diffraction

Figure 3:
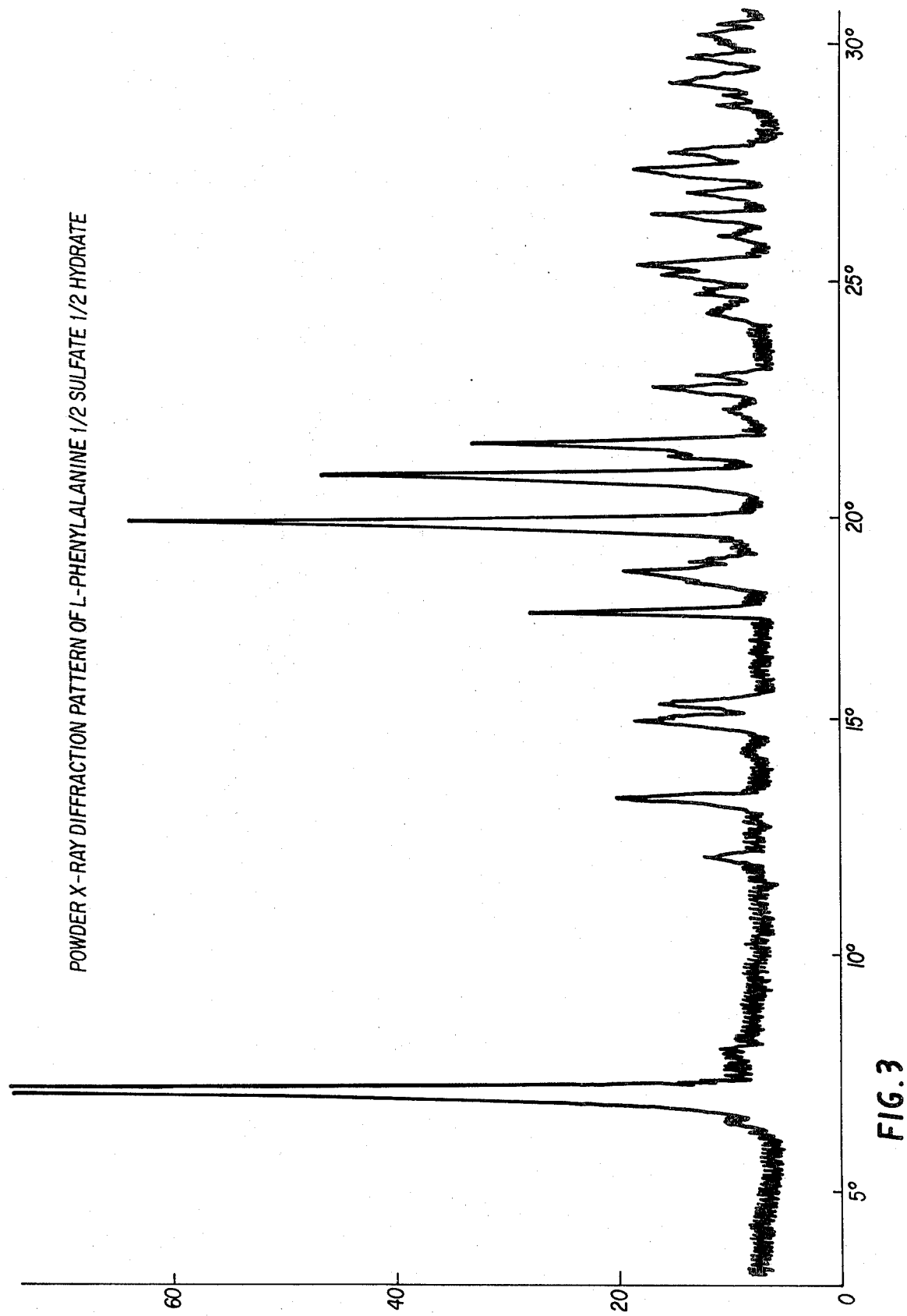

The powder X-ray diffraction of the crystals using the Cu-Kα line is shown in FIG. 3.

6. Solubility

Figure 4:
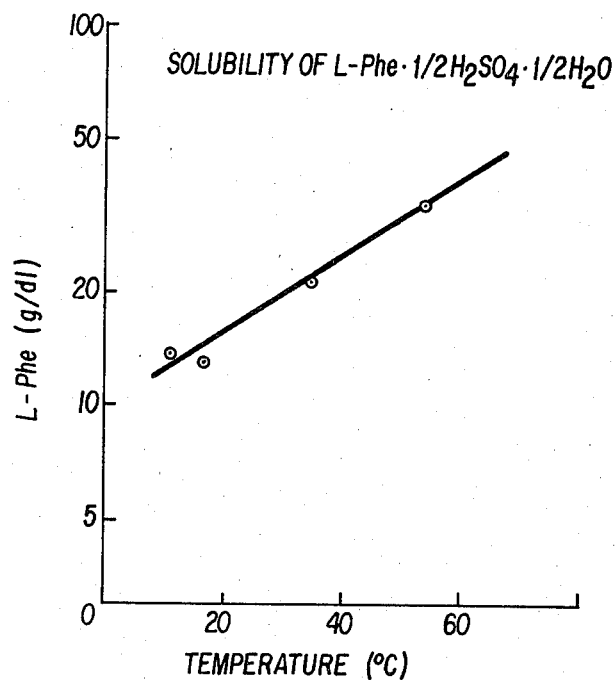

Solubility of the crystals in water is shown in FIG. 4.
The ordinate of the figure indicates L-phenylalanine concentration in units of g/dl.

The crystals are very slightly soluble in ethanol and practically insoluble in ether.

7. Color: Colorless

8. Shape of Crystal: Usually in column.

Such L-phenylalanine ½ sulfate ½ hydrate crystals may form at a pH of about 0.5 to about 1.7.

According to the invention, the sulfate salt of L-phenylalanine will crystallize from a solution of L-phenylalanine when the molar ratio of sulfate ion to L-phenylalanine ($SO_4$/Phe) is greater than 0.5, and usually when the ratio is between 0.5 and 1.0.

Crystallization may preferably be carried out by cooling, since the temperature gradient of the solubility of L-phenylalanine ½ sulfate is steep. However, concentration crystallization may also be employed. When L-phenylalanine ½ sulfate ½ hydrate is crystallized by cooling, for example, a nearly saturated solution of L-phenylalanine ½ sulfate at 50° to 80° C. is first prepared. The solution is then gradually cooled. Seed crystals are added, if necessary, when the solution becomes saturated or supersaturated. The suspension of crystals so produced is further cooled to about 5° to 30° C., and supersaturation is avoided by keeping the suspension at the desired temperature for about 30 minutes to 2 hours. Precipitated crystals are then separated according to conventional means.

This ½ hydrate crystal may be crystallized from a wide variety of solutions containing L-phenylalanine. However, since this crystal has the capability of eliminating impurities derived from fermentation broths of L-phenylalanine, employment of crystallization of the ½ hydrate crystals from solutions present during the processes of recovering L-phenylalanine from fermentation broths is most preferable. Examples of such solutions include L-phenylalanine fermentation broth itself, a cell-free solution thereof, an eluate produced from an ion-exchange resin or decolorization resin on which L-phenylalanine has previously been adsorbed by passing through a layer of such resin the fermentation broth or the cell-free solution thereof, a mother liquor of crude crystals produced from the fermentation broth or the above eluate, and the solution of the above crude crystals. Among the impurities derived from the fermentation broth, L-tyrosine has been particularly difficult to remove; however, tyrosine can easily be removed by the crystallization of L-phenylalanine as its ½ sulfate.

The solubility of L-phenylalanine ½ sulfate in a mother liquor depends on the kind and amount of the impurities present; accordingly, the solubility is preferably measured with reference to the solution of each process.

Since solubility of L-phenylalanine is considerably lower than that of the ½ sulfate, crystallization of L-phenylalanine per se is employed in a process where the crystallization yield is important. For example, when crude L-phenylalanine is directly recovered by crystallization from a fermentation broth, crystallization of L-phenylalanine per se is employed, because recovery of L-phenylalanine from the mother liquor of the crude crystals is economically disadvantageous.

Additionally, since pure L-phenylalanine is usually sold in the free form, the crystallization of L-phenylalanine per se is of necessity employed as the final crystallization step of any purification process. In this case, when crystallization of the ½ sulfate instead of the free form is employed before the final crystallization process, the number of crystallization steps can be reduced. Crystallization of the ½ sulfate is thereby effectively utilized to obtain better yields of pure L-phenylalanine.

Figure 5:
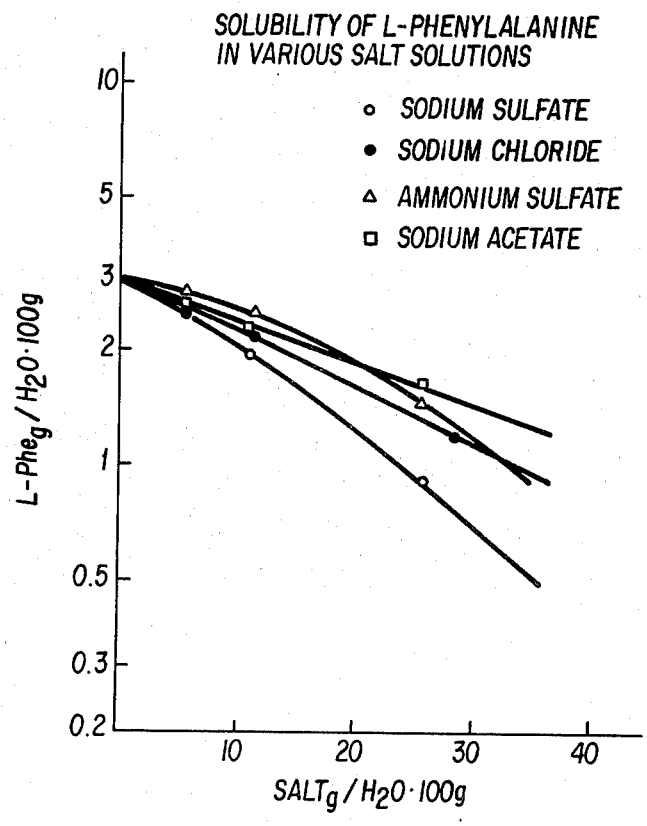

When the free form is crystallized, it is difficult to separate the mother liquor sufficiently from the crystals because of the flake-like shape of the crystals. Accordingly, in order to make isolation and purification by crystallization effective, lowering the solubility of L-phenylalanine is preferable to concentrating the crystallization solution. When sodium sulfate is added to a solution of L-phenylalanine, solubility of L-phenylalanine is extremely lowered by the salting-out effect, thereby increasing the crystallization yield. Influences of various salts on the solubility of L-phenylalanine were measured and are shown in FIG. 5. In the figure, open circles (○) indicate sodium sulfate, black circles ( • ) indicate solium chloride, triangles (△) indicate ammonium sulfate, and squares (□) indicate sodium acetate. As can be seen from the figure, the solubility of L-phenylalanine is lowest in the presence of sodium sulfate. When lowering the solubility of L-phenylalanine is desired, a concentration of sodium sulfate higher than 10 g/100 g water is preferable. The whole or a part of the sodium sulfate may be supplied by contacting the sulfate ions of L-phenylalanine ½ sulfate with sodium hydroxide or a sodium salt capable of producing sodium sulfate by contacting with the L-phenylalanine ½ sulfate. Such salts include sodium carbonate.

When crystals of free L-phenylalanine are produced from the ½ sulfate for commercial use, the ½ sulfate crystals are first dissolved in water. Then, the sulfate ions are removed from the solution by using weakly basic anion-exchange resin, or the solution is neutralized with an alkali such as sodium hydroxide. The resin- or alkali-treated solution is decolorized, if necessary, and concentrated or cooled to crystallize L-phenylalanine crystals. Alternatively, commmerically suitable crystals may be produced without concentration and cooling. In this case, a solution of the ½ sulfate is first decolorized and then neutralized to crystallize L-phenylalanine crystals. If sodium sulfate is in any event added to the decolorized solution, the separated crystals of L-phenylalanine must be washed sufficiently with water.

Anhydrous L-phenylalanine ½ sulfate crystals may be produced by standard techniques, for example, by heating the ½ sulfate crystals at 110° C. for 12 hours.

The above disclosure generally describes the present invention. A more complete understanding can be obtained by reference to the following specific examples, which are provided herein for purposes of illustration only and are not intended to be limiting unless otherwise specified.

EXAMPLE 1

93.8 Milliliters of pure water and 26.2 g of sulfuric acid were added to 80 g of L-phenylalanine, and the L-phenylalanine was entirely dissolved at 80° C. The solution was cooled to 45° C., and a few L-phenylalanine ½ sulfate ½ hydrate crystals were added as seed crystals. The seeded solution was then gradually cooled and moderately stirred at 30° C. for 20 hours. The resulting crystals were centrifuged and collected (79.5 g). The crystals were washed with water (80 g) and dried at room temperature under reduced pressure. The characteristics of the crystals recovered in this experiment are discussed above.

EXAMPLE 2

An L-phenylalanine fermentation broth was passed over a column of a strongly acidic cation-exchange resin, thereby adsorbing L-phenylalanine on the resin. The adsorbed L-phenylalanine was eluted with aqueous ammonia, and the eluate was concentrated. The pH of the concentrate was adjusted to the value given in the following table by using sulfuric acid. The concentrate was then further concentrated. The solution for crystallization so prepared was gradually cooled and allowed to stand overnight. The resulting crystals were filtered and washed with a small amount of water. Experimental conditions and results are shown in the following table. The X-ray diffraction pattern of Run No. 1 crystals was measured by the powder method, which confirmed that these crystals were identical with those of Example 1.

| Run No. | 1 | 2 (Control) |
|---|---|---|
| Solution for Crystallization | | |
| L-Phe concentration (wt. %) | 23.3 | 6.6 |
| pH | 1.5 | 5.5 |
| Final temperature (°C.) | 20 | 35 |
| Nitrogen purity* (%) | 65 | 65 |
| Tyr/Phe (wt. %) | 4.0 | 4.0 |
| Crystals | | |
| Nitrogen purity (%) | 96 | 92 |
| Tyr/Phe (wt. %) | 1.1 | 3.2 |
| Color (−log T at 430 nm)/Phe | 0.11 | 0.25 |
| SO$_4$/Phe (M.R.) | 0.51 | 0 |
| Crystallization yield (%) | 48 | 51 |

*Nitrogen of L-Phe/(Total nitrogen−Ammonia nitrogen)

EXAMPLE 3

Filter aid was added to an L-phenylalanine fermentation broth, and the fermentation broth was filtered. The filtrate was concentrated at 60° C. under reduced pressure until crystals formed in the concentrate. The concentrate was gradually cooled to 35° C., and crystals were then separated. Water and sulfuric acid were added to the crystals, and the crystals were dissolved at 80° C. Both pH and concentration of the solution were adjusted to the values described in the following table. The crystallization solution so prepared was gradually cooled and allowed to stand overnight. The resulting crystals were filtered and washed with a small amount of water. Experimental conditions and results are shown in the following table. The X-ray diffraction pattern of Run No. 1 crystals was measured by the powder method, thereby confirming that these crystals are identical with those of Example 1.

| Run No. | 1 | 2 (Control) |
|---|---|---|
| Solution for Crystallization | | |
| L-Phe concentration (wt. %) | 16.7 | 5.9 |
| pH | 1.5 | 5.5 |
| Final temperature (°C.) | 20 | 35 |
| Nitrogen purity (%) | 48 | 48 |
| Tyr/Phe (Wt. %) | 3.5 | 3.5 |
| Crystals | | |
| Nitrogen purity (%) | 95 | 90 |
| Tyr/Phe (wt. %) | 0.55 | 3.6 |
| Color (−log T at 430 nm)/Phe | 0.14 | 0.50 |
| $SO_4$/Phe (M.R.) | 0.51 | 0 |
| Crystallization yield (%) | 46 | 44 |

EXAMPLE 4

Filter aid was added to an L-phenylalanine fermentation broth, and the fermentation broth was then filtered. The filtrate was divided into three equal parts, and sodium sulfate was added to each part of the filtrate. Each filtrate was then evaporated to a predetermined concentration at 60° C. under reduced pressure. The crystallization solutions so produced were gradually cooled to 35° C. and allowed to stand at 35° C. overnight. The resulting crystals were separated by centrifugcation. Experimental conditions and results are shown in the following table.

| Run No. | 1 | 2 | 3 |
|---|---|---|---|
| Solution for Crystallization | | | |
| L-Phe concentration (wt. %) | 10.7 | 10.5 | 10.8 |
| Crystals | | | |
| Nitrogen purity (%) | 83 | 84 | 83 |
| Crystallization yield (%) | 91 | 86 | 78 |
| Mother Liquor | | | |
| L-Phe concentration (wt. %) | 1.1 | 1.7 | 2.8 |
| $Na_2SO_4$ concentration (g/100g $H_2O$) | 21 | 13 | 6 |

Each batch of crystals was dissolved in water at 50° C., giving three batches of 3 g/dl L-phenylalanine solution. Sulfuric acid, 0.55 mole per mole of L-phenylalanine, was added to each solution, and the solutions were concentrated at 60° C. under reduced pressure until the L-phenylalanine concentration was 30 wt. %. The pH values of the concentrates were all about 1.1. The concentrates were gradually cooled to 20° C. and allowed to stand at 20° C. overnight. The resulting crystals were separated and washed with a small amount of water. Crystallization yields were 70 to 72%, and nitrogen purities were 96 to 97%. The molar ratio $SO_4$/Phe of the crystals were 0.49 to 0.51, and the X-ray diffraction patterns of the crystals of all batches indicated that they were all L-Phe.½ $H_2SO_4$.½ $H_2O$ crystals.

The three batches of ½ sulfate crystals were separately dissolved in water, and each solution was decolorized by activated charcoal powder. The decolorized solutions were neutralized with sodium hydroxide, thereby depositing L-phenylalanine crystals. The crystals were separated and washed with water. The dried crystals of each batch were all pure white, and nitrogen purities of the crystals were 99.5 to 99.8%.

EXAMPLE 5

An L-phenylalanine fermentation broth was passed over a column of a strongly acidic cation-exchange resin, thereby adsorbing L-phenylalanine on the resin. The adsorbed L-phenylalanine was eluted with aqueous ammonia, and the eluate was concentrated. Sulfuric acid was added to the concentrate, and the concentrate was further concentrated. Then, the concentrate was cooled, and L-phenylalanine ½ sulfate ½ hydrate crystals formed.

The ½ sulfate crystals were divided into three equal parts, and sodium sulfate and water were added to two parts. To the remaining part, only water was added. Each part was then heated at 60° C., and the crystals were entirely dissolved.

The crystallization solutions so prepared were adjusted to pH 5.5 using sodium hydroxide while the temperature was maintained at 60° C., and then gradually cooled to 35° C. with stirring. The slurries so produced were allowed to stand overnight and the resulting crystals were separated. The crystals were washed with a small amount of water. The experimental conditions and results are shown in the following table.

| Run No. | 1 | 2 | 3 (Control) |
|---|---|---|---|
| Solution for Crystallization | | | |
| L-Phe concentration (wt. %) | 13.5 | 13.5 | 13.4 |
| pH | 1.7 | 1.7 | 1.7 |
| $Na_2SO_4$ concentration (wt. %) | 10 | 5 | 0 |
| Nitrogen purity (%) | 94 | 94 | 94 |
| Crystals | | | |
| Nitrogen purity (%) | 99 | 98 | 99 |
| Crystallization yield (%) | 93 | 88 | 81 |
| Mother Liquid | | | |
| L-Phe concentration (wt. %) | 1.0 | 1.6 | 2.4 |
| $Na_2SO_4$ concentration (g/100g $H_2O$) | 20 | 13 | 7 |

The invention now being fully described, it will be apparent to one of ordinary skill in the art that many changes and modifications can be made thereto without departing from the spirit or scope of the invention as set forth herein.

What is claimed is:

1. A process for recovering L-phenylalanine from a fermentation broth containing L-phenylalanine, which comprises adjusting the molar ratio of sulfate ion to L-phenylalanine to greater than 0.5, forming L-phenylalanine ½ sulfate in solution and recovering L-phenylalanine crystals from said fermentation broth or from a solution thereof produced during said recovery process.

2. The process of claim 1, wherein said L-phenylalanine ½ sulfate has a half molecule of water of crystallization.

3. The process of claim 1 or claim 2, wherein said fermentation broth or said solution produced during said process of recovering L-phenylalanine contains L-tyrosine.

4. The process of claim 1, 2 or claim 3, wherein said process of recovering L-phenylalanine crystals from a L-phenylalanine solution containing sodium sulfate comprises using separation techniques of crystallization, ion-exchange, eluting, cooling, neutralization, decolorization, saturation, heating, washing, filtering, drying or combinations thereof.

5. The process of claim 4, wherein said sodium sulfate is produced by contacting said L-phenylalanine ½ sulfate with sodium hydroxide or a sodium salt capable of producing sodium sulfate by contacting with said L-phenylalanine ½ sulfate.

6. The process of claim 4, wherein the concentration of said sodium sulfate is higher than 10 g/100 g water.

* * * * *